(12) United States Patent
Rao et al.

(10) Patent No.: US 11,001,871 B2
(45) Date of Patent: May 11, 2021

(54) METHOD FOR PRODUCING 9ALPHA-HYDROXY ANDROSTANE-4-ALKENE-3,17-DIKETONE BY ENZYMATIC CONVERSION

(71) Applicant: Jiangnan University, Wuxi (CN)

(72) Inventors: Zhiming Rao, Wuxi (CN); Zongyan Sha, Wuxi (CN); Xian Zhang, Wuxi (CN); Taowei Yang, Wuxi (CN); Meijuan Xu, Wuxi (CN)

(73) Assignee: Jiangnan University, Wuxi (CN)

( * ) Notice: Subject to any disclaimer, the term of this patent is extended or adjusted under 35 U.S.C. 154(b) by 192 days.

(21) Appl. No.: 16/256,001

(22) Filed: Jan. 24, 2019

(65) Prior Publication Data
US 2019/0185899 A1    Jun. 20, 2019

Related U.S. Application Data

(63) Continuation of application No. PCT/CN2018/081871, filed on Apr. 4, 2018.

(30) Foreign Application Priority Data

Dec. 15, 2017  (CN) .......................... 201711352434.8

(51) Int. Cl.
*C12P 33/06* (2006.01)
*C12N 9/02* (2006.01)

(52) U.S. Cl.
CPC ............ *C12P 33/06* (2013.01); *C12N 9/0008* (2013.01); *C12N 9/0077* (2013.01)

(58) Field of Classification Search
None
See application file for complete search history.

(56) References Cited

FOREIGN PATENT DOCUMENTS

| | | |
|---|---|---|
| CN | 104232722 A | 12/2014 |
| CN | 106119180 A | 11/2016 |
| WO | 0131050 A1 | 5/2001 |

OTHER PUBLICATIONS

Zhang, Xian; et al; "A Novel 3-Phytosterone-9[alpha]-Hydroxylase Oxygenation Component and Its Application in Bioconversion of 4-Androstene-3,17-Dione to 9[alpha]-Hydroxy-4-Androstene-3,17-Dione Coupling with A NADH Regeneration Formate Dehydrogenase" Molecules, 24, 2534, 2019 (Year: 2019).*

Guie Wang et al., Enhanced expression of 3-steroid-9α-hydroxylase gene in mycobacterium, Chinese Journal of Pharmaceutical Biotechnology, Oct. 15, 2016 (Oct. 15, 2016), No. 5, vol. 23, ISSN: 1005-8915 Abstract.

* cited by examiner

*Primary Examiner* — David W Berke-Schlessel
(74) *Attorney, Agent, or Firm* — IPro, PLLC

(57) ABSTRACT

The present disclosure discloses a method for producing 9α-hydroxy androstane-4-alkene-3,17-diketone by enzymatic conversion, and belongs to the fields of gene engineering and enzyme engineering. According to the present disclosure, oxidation subunit KshA, reduction subunit KshB and unknown active subunit KshC of 3-ketosteroid-9α-hydroxylase sourcing from *Mycobacterium* sp. Strain VKM Ac-1817D are successfully expressed in *E. coli* BL21, and KshC is identified as an oxidation subunit, the enzyme activity of which is far higher than that of KshA. BL21/pET-28a(+)-fdh constructed in the laboratory is used for expressing formate dehydrogenase (FDH), and by using crude enzyme liquid of KSH (KshB+KshC) and FDH engineering bacteria as a biocatalyst and a steroidal compound (AD) as a substrate, optimum reaction temperature is determined as 30° C. and optimum pH is determined as 7.0. In optimum conditions, AD is converted to produce a product 9-OH-AD, and within 20 hours, the output of 9-OH-AD is 4.7 g/L, and the molar conversion rate reaches 96.7%. According to the present disclosure, in production of 9-OH-AD, coupling of a 3-ketosteroid-9α-hydroxylase hydroxylation system and a coenzyme recycling system is realized, and the method has the advantages of being high in efficiency, low in cost, green, environmentally friendly and the like.

11 Claims, No Drawings
Specification includes a Sequence Listing.

METHOD FOR PRODUCING 9ALPHA-HYDROXY ANDROSTANE-4-ALKENE-3,17-DIKETONE BY ENZYMATIC CONVERSION

TECHNICAL FIELD

The present disclosure relates to a method for producing 9α-hydroxy androstane-4-alkene-3,17-diketone by enzymatic conversion, and belongs to the fields of gene engineering and enzyme engineering.

BACKGROUND

Steroidal compounds are a kind of important natural organic compound widely existing in an organism tissue, and because the steroidal medicine has multiple physiological functions and gives play to a unique curative effect, the steroidal medicine is widely applied clinically, is a second major category of medicine ranked only second only to antibiotics, and has an annual growth rate of 15% or above. The steroidal compounds generally have a series of unique physiological functions, which is mainly because of difference of substituent group, double bond position or spatial configuration on the mother nucleus of the steroidal compounds. The steroidal compounds possess similar structures, are complicated in structure and large in quantity, and commonly exist in animal and plant tissues and certain microorganisms, and what are relatively common include cholesterol, cholic acid, sex hormone, adrenal cortex hormone, progesterone and androsterone, etc. in animal tissues, diosgenin and sitosterol, etc. in plants, and ergosterol, etc. in yeast cells.

Due to existence of 9-hydroxyl in chemical structure of 9α-hydroxy androstane-4-alkene-3,17-diketone (9α-OH-AD), a C9, 11-double band system may be formed by virtue of a conventional steroid chemical synthesis means, so as to conveniently introduce a functional hydroxyl essential for forming glucocorticoid from halogen atom at the C9 site. 9α-OH-AD is an important steroid medicine intermediate, the 9α site is taken as the hydroxylated site, and after simple halogenation reaction, halogen substituents such as F or Cl may be introduced, so as to effectively promote the pharmacological function of certain adrenal cortical hormones (such as dexamethasone, betamethasone, mometasone furoate and beclomethasone), implementation of the technological process can fundamentally solve the problems of low C11α-hydroxylation conversion rate and plenty of byproducts in the present industrial production, and thus having extremely high commercial value.

3-ketosteroid-9α-hydroxylase (KSH) is a key enzyme for steroid microbial metabolism, and it widely exists in microorganisms, such as *Rhodococcus, Nocardia, Arthrobacter* and *Mycobacterium*. A 3-ketosteroid-9α-hydroxylase system is bi-component enzyme, is formed by KshA (3-ketosteroid-9α-hydroxylase oxidase) and KshB (3-ketosteroid-9α-hydroxylase reductase), and KshA and KshB are respectively encoded with genes kshA and kshB, this is verified in *Rhodococcus erythropolis* SQ1 at the earliest, and shown by gene knockout research performed on *Rhodococcus erythropolis* SQ1, kshA and kshB are both necessary components for KSH expression. KshB is a reducing component of the 3-ketosteroid-9α-hydroxylase system, which is in charge of transferring reducing power coming from NADH to KshA, so as to enable KshA to return to the reduction state from the oxidization state and constantly generate hydroxylation reaction at a corresponding position of the steroid, in addition, KshB is multifunctional enzyme, and it not only plays a role in the 3-ketosteroid-9α-hydroxylase system, but also plays an important role in other places, needing reducing power, in organisms.

FDH is capable of catalyzing formic acid decomposition to produce $CO_2$, meanwhile reduces $NAD^+$ to produce NADH, and can be combined with the 3-ketosteroid-9α-hydroxylase system. A great deal of researches show that FDH is a best NADH regeneration enzyme, and has unique advantages in synthesis of chiral compounds: (1) FDH catalytic reaction is irreversible, and main reaction product recovery rate can be up to 99% or above; (2) substrate formate ions are relatively cheap, product $CO_2$ escapes from the system easily, and the purification and separation steps are simplified; (3) FDH has a relatively wide tolerance, and in this reaction, only one byproduct-$CO_2$ is produced, while $CO_2$ has no influence on the activity of any enzyme, and the reaction is complete, and meanwhile, as a gas, $CO_2$ easily escapes from the reaction system.

SUMMARY

In order to solve the aforementioned problems, based on different catalytic functions of KSH and FDH, a method of converting androstane-4-alkene-3,17-diketone (AD) into 9-OH-AD with crude enzyme liquid is successfully established, and therefore, coupling of a hydroxylation system and a coenzyme regeneration system is realized.

One objective of the present disclosure is to provide a composition for producing 9α-hydroxy androstane-4-alkene-3,17-diketone by converting androstane-4-alkene-3,17-diketone, wherein the composition contains a 3-ketosteroid-9α-hydroxylase mixed enzyme solution formed by 3-ketosteroid-9α-hydroxylase reduction subunit KshB and 3-ketosteroid-9α-hydroxylase oxidation subunit KshC.

In one embodiment of the present disclosure, the composition also contains coenzyme $NA^+$, NADH and formate dehydrogenase or any combination of the three.

In one embodiment of the present disclosure, the amino acid sequence of the 3-ketosteroid-9α-hydroxylase reduction subunit KshB is SEQ ID NO.4.

In one embodiment of the present disclosure, the amino acid sequence of the 3-ketosteroid-9α-hydroxylase oxidation subunit KshC is SEQ ID NO.5.

In one embodiment of the present disclosure, the composition is formed by the 3-ketosteroid-9α-hydroxylase mixed enzyme solution formed by 3-ketosteroid-9α-hydroxylase reduction subunit KshB and 3-ketosteroid-9α-hydroxylase oxidation subunit KshC, NADH and formate dehydrogenase.

In one embodiment of the present disclosure, the additive proportion of the 3-ketosteroid-9α-hydroxylase oxidation subunit KshC to the 3-ketosteroid-9α-hydroxylase reduction subunit KshB to the formate dehydrogenase is 1-10:1-10:1-10 according to enzyme activity.

In one embodiment of the present disclosure, the additive amount of NADH is 0.01-1 mol/L.

The second objective of the present disclosure is to provide a preparation method of the composition, wherein the method specifically comprises the following steps:

(1) by taking the nucleotide sequence as shown in SEQ ID NO.2 as a template, amplifying to obtain a gene for encoding 3-ketosteroid-9α-hydroxylase reduction subunit KshB, and cloning the gene to an *escherichia coli* expression vector pET-28a to obtain recombinant plasmid pET-28a-kshB;

(2) by taking the nucleotide sequence as shown in SEQ ID NO.3 as a template, amplifying to obtain a gene for encoding 3-ketosteroid-9α-hydroxylase oxidation subunit KshC, and cloning the gene to an *escherichia coli* expression vector pET-Duet1(+) to obtain recombinant plasmid pET-Duet1 (+)-kshC;

(3) respectively converting the recombinant plasmids obtained in step (1) and step (2) into *escherichia coli* to obtain recombinant *escherichia coli* BL21/pET-28a(+)-kshB and BL21/pET-Duet1(+)-kshC; and (4) fermenting with the recombinant *escherichia coli* obtained in step (3) to obtain a 3-ketosteroid-9α-hydroxylase mixed enzyme solution formed by 3-ketosteroid-9α-hydroxylase reduction subunit KshB and 3-ketosteroid-9α-hydroxylase oxidation subunit KshC.

The third objective of the present disclosure is to provide a method for increasing the efficiency of converting androstane-4-alkene-3,17-diketone to produce 9α-hydroxy androstane-4-alkene-3,17-diketone, wherein the method performs biotransformation by using the composition as a catalyst.

The fourth objective of the present disclosure is to provide application of the composition of in the field of medicines.

Beneficial Effects of the Disclosure

According to the present disclosure, a molecular technique is used for cloning oxidation subunit gene kshA, reduction subunit gene kshB and unknown active subunit gene kshC of 3-ketosteroid-9α-hydroxylase sourcing from *Mycobacterium* sp. Strain VKM Ac-1817D, recombinant expression vectors pET-28a(+)-kshA, pET-28a(+)-kshB and pET-Duet1(+)-kshC are constructed and are converted into *E. coli* BL2 by a chemical method, genetic engineering bacteria BL21/pET-28a(+)-kshA, BL21/pET-28a(+)-kshB and BL21/pET-Duet1(+)-kshC are successfully constructed, and KshC is identified as an oxidation subunit. BL21/pET-28a(+)-fdh already constructed in this laboratory is utilized, and it is found in an enzyme activity determination result that enzyme activities of KSH (KshB+KshC) and FDH are respectively 5.66 U/mL and 0.25 U/mL. Based on the obtained genetic engineering bacteria, crude enzyme liquid of each strain of engineering bacterium is obtained by cell disruption, and is used for converting AD to produce 9-OH-AD for preliminary research, and within 20 hours, the output of 9-OH-AD is 4.7 g/L, and the molar conversion rate reaches 96.7%.

DETAILED DESCRIPTION

A KSH determination system includes: 105 μM of NADH, 200 μM of substrate AD (dissolved in 100% isopropyl alcohol), 50 m of Tris-HCL (200 μL, pH7.0), and KSH enzyme. Therefore, the activity is defined as the enzyme amount needed for oxidizing a steroid substrate AD in 1 min, and is expressed as enzyme amount needed for oxidizing 1 nmol of NADH in 1 min, and the specific activity unit is nmol $min^{-1}$ $mg^{-1}$ (U/mg).

An FDH enzyme activity determination method comprises the following steps: preparing 17 mg·$mL^{-1}$ of sodium formate solution (pH 7.5) and 3 mg·$mL^{-1}$ of $NAD^+$ solution, taking 1.48 mL of sodium formate solution and putting into a quartz cuvette, sequentially adding 80 μL of $NAD^+$ solution and 10 μL of crude enzyme liquid, detecting light absorption value change of each minute at 340 nm, wherein enzyme activity defining unit is enzyme amount needed for catalyzing 1 μmol of $NAD^+$ to be converted into NADH in 1 min.

HPLC analysis: AD and 9-OH-AD both have characteristic absorption peaks at ultraviolet wavelength of 254 nm, and therefore, an HPLC method is adopted to formulate 10 μL, and the flow velocity is 1.0 mL/min.

LB culture medium: peptone 10 g/L, yeast extract 5 g/L, and NaCl 10 g/L (2% agar powder is added to a solid culture medium).

Example 1: 3-Ketosteroid-9α-Hydroxylase Primer Design

According to kshA gene sequence (SEQ ID NO.1) in a whole genome nucleotide sequence of *Mycobacterium* sp. Strain VKM Ac-1817D in NCBI, PCR primers P1 and P2 (SEQ ID NO.6 and SEQ ID NO.7) of 3-ketosteroid-9α-hydroxylase oxidation subunit KshA are designed.

P1:
5'-CGGGATCCATGACGACTGAGCACGCCGG-3' (BamH I)

P2:
5'-CCCAAGCTTTCAGCTTGATTGAGCGGTTTC-3' (Hind III)

According to kshB gene sequence (SEQ ID NO.2) in a whole genome nucleotide sequence of *Mycobacterium* sp. Strain VKM Ac-1817D in NCBI, PCR primers P3 and P3 (SEQ ID NO.8 and SEQ ID NO.9) of 3-ketosteroid-9α-hydroxylase reduction subunit KshB are designed.

P3:
5'-CGGGATCCATGACTGATGAACCGTTAGGTAG-3' (BamH I)

P4:
5'-CCCAAGCTTTCACTCGTCGTAGGTCACCTC-3' (Hind III)

According to kshC gene sequence (SEQ ID NO.3) in a whole genome nucleotide sequence of *Mycobacterium* sp. Strain VKM Ac-1817D in NCBI, PCR primers P5 and P6 (SEQ ID NO.10 and SEQ ID NO.11) of 3-ketosteroid-9α-hydroxylase KshC are designed.

P5:
5'-CGGGATCCGATGGCCGGTCTGAACAACGATAG-3' (BamH I)

P6:
5'-CCCAAGCTTTCAGCCGCTGGCCGGGGCGGCC-3' (Hind III)

Example 2: Clone of 3-Ketosteroid-9α-Hydroxylase Genes kshA, kshB and kshC

By taking synthesized DNA as a template, PCR amplification is performed by using the primers provided above, and the amplification conditions are as follows: pre-denaturation at 94° C., 5 min, one cycle; denaturation at 94° C., 1 min, re-firing at 58° C., 1 min, extension at 72° C., 34 cycles; final extension for 10 min at 72° C. A PCR amplification system: template 1 μL, up-stream and down-stream primers respectively 0.4 μL, dNTP Mix 4 μL, 10×Ex Taq Buffer 5 μL, sterile double distilled water 37 μL, and Ex Taq DNA polymerase 1 μL. A gel extraction kit is adopted to perform purification and recycling on the PCR product, and the concentration of the recycled product is tested by electrophoresis. The recycled product is stored in a 1.5 ml centrifugal tube, and is preserved in a refrigerator at 20° C. for later use. The recycled product is connected with pMD18-T Vector, the connection product converts *E. coli* JM109, the conversion product is coated on an LB slab with ampicillin resistance, the obtained product is cultured at 37° C. and stays overnight, a bacterial colony is picked to a 10 ml liquid LB culture medium, plasmids are extracted after staying overnight on a shaking table and culturing at 37° C. and are named as pMD18 T-kshA, pMD18 T-kshB and pMD18 T-kshC, and after connection is verified to be successful by enzyme digestion, glycerinum is added until the concentration is 15%~20% (w/v), and the product is preserved in a refrigerator at −70° C.

Example 3: Construction of Recombinant Expression Vectors pET-28a(+)-kshA, pET-28a(+)-kshB and pET-Duet1(+)-kshC Plasmids pMD18 T-kshA, pMD18 T-kshB, pMD18 T-kshC and pET-28a (+), pET-Duet1(+) stored in *E. coli* jM109 are extracted, and double enzyme digestion is performed respectively with BamH I/Hind III, and connection is performed after the product is recycled by using the gel extraction kit, and the connection system is as follows: target gene enzyme-digested product 7 μL, pET-28a (+) or pET-Duet1(+) enzyme-digested product 1 μL, T4DNA ligase buffer 111 L and T4DNA ligase 1μL, and the connection system is connects by staying overnight at 16° C. Connected recombinant plasmids pET-28a(+)-kshA, pET-28a(+)-kshB and pET-Duet1(+)-kshC are converted to competent *E. coli* jM109, and positive bacterial colony is picked by using LB kanamycin resistant and ampicillin resistant culture medium. Plasmids are extracted after staying overnight on a shaking table and culturing at 37° C. and are named as pET-28a(+)-kshA, pET-28a(+)-kshB and pET-Duet1(+)-kshC, and after it is verified to be correct by enzyme digestion, glycerinum is added until the concentration is 15%~20% (w/v), and the product is preserved in a refrigerator at −70° C.

Example 4: Conversion of *E. coli* BL21 with Recombinant Plasmids pET-28a(+)-kshA, pET-28a(+)-kshB and pET-Duet1(+)-kshC

*E. coli* BL21 competence preparation: (1) picking newly activated single colony on the LB slab, inoculating into 10 mL of LB liquid culture medium for culturing for about 12 h, and then inoculating the bacterial suspension into 50 mL of LB liquid culture medium in the inoculation amount of 1% for culturing for 2-3 h, until $OD_{600}$ reaches about 0.5. (2) Putting the bacterial solution into an ice-water bath for 15 min, so that the bacterial solution is rapidly cooled. (3) Packaging the bacterial solution into a plurality of 1.5 mL centrifugal tubes separately, centrifuging for 1 min at 8000 rpm and then abandoning the liquid supernatant, and washing cells for 2-3 times with 1M of $CaCl_2$ solution. (4) Preserving the cleaned bacterial solution for a long time at −40° C. after being suspended with 80 μL of $CaCl_2$ and 40 μL of 50% glycerinum.

Conversion: 10 μL of recombinant plasmids pET-28a(+)-kshA, pET-28a(+)-kshB and pET-Duet1(+)-kshC are respectively added into two tubes of *E. coli* BL21 competent cells, the product is uniformly mixed slightly and then placed on ice for 45 min, then is subjected to water bath heat shock for 90 s at 42° C. and then placed on ice for 5 min, then is added into 800 μL of LB liquid culture medium and then being cultured for 1 h at 37° C., and is centrifuged for 1 min at 8000 rpm, the liquid supernatant is abandoned, the rest bacterial solution is coated to the LB slab with kanamycin resistance and ampicillin resistance, and after being cultured at 370° C., positive bacterial colony is picked, and plasmids are extracted for enzyme digestion verification, so as to obtain recombinant bacteria BL21/pET-28a(+)-kshA, BL21/pET-28a(+)-kshB and BL21/pET-Duet1(+)-kshC.

Example 5: Functional Identification of KshC and Determination of Activity of 3-Ketosteroid-9α-Hydroxylase Recombinant bacteria BL21/pET-28a(+)-kshA and BL21/pET-28a(+)-kshB constructed in Example 4 as well as original strain BL21/pET-28a(+) are respectively inoculated into 10 ml of LB culture medium containing kanamycin, BL21/pET-Duet1(+)-kshC is inoculated into 10 ml of LB culture medium containing ampicillin, the product stays overnight in shaking culture at 37° C., in the next day, the product is transferred into 50 mL of LB culture medium according to an inoculum size of 1%, after culture is performed for 2 h at 37° C. and when $OD_{600}$ is 0.8, IPTG with final concentration of 0.8 mM is added, the product is induced for 9 h at 28° C., then the bacterial solution is centrifuged for 10 min at 10000 r/min at 4° C., a phosphate buffer ($Na_2HPO_4$—$NaH_2PO_4$) with pH of 7.5 is used for washing for twice, and finally, 5 ml of phosphate buffer with pH of 7.5 is used for suspension. Crude enzyme liquid is prepared by ultrasonic disruption processing.

A KSH determination system contains 105 μM of NADH, 200 μM of substrate AD (dissolved in 100% isopropanol), 50 m of Tris-HCL (200 μL, pH7.0), and KSH enzyme (including oxidation subunit and reduction subunit). By verification, KshC is the oxidation subunit, and in the condition of ensuring same concentration of induction culture cells, enzyme activity with co-action of KshB crude enzyme liquid+KshC crude enzyme liquid with same additive amount is 30.7 U/mL, which is far higher than the KSH enzyme activity with co-action of KshA and KshB crude enzyme liquid, the former is 5.4 times of the latter, however, KSH enzyme activity is not detected in original bacterium *E. coli* BL21/pET-28a(+), and thus realizing out of nothing of enzyme activity of 3-ketosteroid-9α-hydroxylase in *E. coli* BL21.

Example 6: Generation of 9-OH-AD by Conversion of 3-Ketosteroid-9α-Hydroxylase

KshA crude enzyme liquid or KshC crude enzyme liquid and KshB crude enzyme liquid obtained in Example 5 are added into 10 mL of conversion system in a proportion of 1:1.5 of enzyme amount to additive amount: 0.1 M of Tris-Hcl buffer solution, pH of 7.0, 0.32 mMol of NADH, 1 $g·L^{-1}$ of substrate AD (firstly dissolved in ethyl acetate) and crude enzyme mixed liquid (KshA+KshB or KshC+KshB), pH is regulated with 20% formic acid and 50% ammonia water, rotation speed is 160 r·min-1, conversion is performed for 20 h at 30° C., and substrate AD and coenzyme NADH need to be supplemented in due time, the result shows that the output of 9-OH-AD in the KshA+KshB crude enzyme liquid conversion system is 0.98 g/L, while the output of 9-OH-AD in the KshC+KshB crude enzyme liquid conversion system is 7.8 g/L. Therefore, oxidation subunit KshC of 3-ketosteroid-9α-hydroxylase has a better effect than KshA.

Example 7: Determination on Activity of *E. coli* BL21/pET-28a(+)-Fdh Formate Dehydrogenase Recombinant bacterium *E. coli* BL21/pET-28a(+)-fdh constructed by the laboratory is inoculated into 10 ml of LB culture medium containing kanamycin, the product is subjected to overnight shaking culture at 37° C., in the next day, the product is transferred into 50 ml of LB culture medium according to an inoculum size of 1%, after culture is performed for 2 h at 37° C. and when $OD_{600}$ is 0.8, IPTG with final concentration of 0.8 mM is added, the product is induced for 9 h at 28° C., then the bacterial solution is centrifuged for 10 min at 10000 r/min at 4° C., ($Na_2HPO_4$—$NaH_2PO_4$) is used for washing for twice, and finally, 5 ml of phosphate buffer with pH of 7.5 is used for suspension. Crude enzyme liquid is prepared by ultrasonic disruption processing.

17 mg/mL of sodium formate solution (pH 7.5) and 3 mg/mL of $NAD^+$ solution are prepared, 1.48 mL of sodium formate solution is taken and put into a quartz cuvette, 80μL of $NAD^+$ solution and 10μL of crude enzyme liquid are sequentially added, light absorption value change of each minute is detected at 340 nm, and enzyme activity defining unit is enzyme amount needed for catalyzing 1 μmol of $NAD^+$ to be converted to NADH in 1 min. It is shown by the result that the enzyme activity of recombinant bacterium *E. coli* BL21/pET-28a(+)-fdh is 0.25 U/m L.

Example 8: Generation of 9-OH-AD by Conversion of AD with 3-ketosteroid-9α-Hydroxylase and Formate Dehydrogenase 3-ketosteroid-9α-hydroxylase and formate dehydrogenase (FDH) crude enzyme liquid obtained by ultrasonication are added into 25 mL of conversion system in a proportion of 1:0.5 according to enzyme activity additive amount: 0.1 M of Tris-Hcl buffer solution, pH of 7.0, containing any one of 10 $g·L^{-1}$ of ammonium formate, 0.25 mmol of $NAD^+$ or NADH, 10 $g·L^{-1}$ of substrate AD (firstly dissolved in ethyl acetate) and crude enzyme mixed liquid (KSH and FDH), pH is regulated with 20% formic acid and 50% ammonia water, rotation speed is 160 $r\,min^{-1}$, conversion is performed for 20 h at 30° C., substrate AD needs to be supplemented in due time, NAD+, NADH or FDH does not need to be supplemented for control experiment, the result is as shown in table 1, and when 3-ketosteroid-9α-hydroxylase is KshC+KshB crude enzyme liquid, and FDH+NADH are added to participate in coenzyme regeneration, the output of 9-OH-AD is 9.7 g/L, and the molar conversion rate is 97%.

To sum up, the obtained output result is as shown in the following table:

TABLE 1

Synthesis of 9α-Hydroxy Androstane-4-Alkene-3,17-Diketone by Adding of Different Enzyme Liquid and Coenzyme

| Enzyme liquid | Type of added coenzyme | Output of 9α-hydroxy androstane-4-alkene-3,17-diketone (g/L) |
|---|---|---|
| KshA + KshB | — | 0.3 ± 0.02 |
| KshC + KshB | — | 2.3 ± 0.05 |
| KshA + KshB | NADH | 1.2 ± 0.04 |
| KshC + KshB | NADH | 7.8 ± 0.11 |
| KshA + KshB | FDH | 0.5 ± 0.03 |
| KshC + KshB | FDH | 2.9 ± 0.06 |
| KshA + KshB | FDH + $NAD^+$ | 0.6 ± 0.02 |
| KshC + KshB | FDH + $NAD^+$ | 4.7 ± 0.07 |
| KshA + KshB | FDH + NADH | 2.6 ± 0.04 |
| KshC + KshB | FDH + NADH | 9.7 ± 0.15 |

What is claimed is:

1. A composition comprising an *Escherichia coli* bacterium comprising genes encoding 3-ketosteroid-9α-hydroxylase reduction subunit KshB and 3-ketosteroid-9α-hydroxylase oxidation subunit KshC.

2. The composition of claim 1, further comprising coenzyme $NAD^+$, NADH, formate dehydrogenase, or a combination thereof.

3. The composition of claim 1, wherein an amino acid sequence of the 3-ketosteroid-9α-hydroxylase reduction subunit KshB is SEQ ID NO:4.

4. The composition of claim 1, wherein an amino acid sequence of the 3-ketosteroid-9α-hydroxylase oxidation subunit KshC is SEQ ID NO:5.

5. The composition of claim 1, wherein the composition further comprises NADH and formate dehydrogenase.

6. The composition of claim 5, wherein the additive proportion of the 3-ketosteroid-9α-hydroxylase oxidation subunit KshC to the 3-ketosteroid-9α-hydroxylase reduction subunit KshB to the formate dehydrogenase is 1-10:1-10:1-10 according to enzyme activity.

7. The composition of claim 5, wherein NADH is present in an amount of 0.01 to −1 mol/L.

8. A method of preparing a composition, wherein the composition comprises 3-ketosteroid-9α-hydroxylase reduction subunit KshB and 3-ketosteroid-9α-hydroxylase oxidation subunit KshC, and wherein the method comprises:
(a) amplifying a nucleotide sequence set forth in SEQ ID NO:2 to obtain a gene encoding 3-ketosteroid-9α-hydroxylase reduction subunit KshB, and cloning the gene encoding 3-ketosteroid-9α-hydroxylase reduction subunit KshB into an *Escherichia Coli* expression vector pET-28a to obtain a recombinant plasmid pET-28a- kshB;
(b) amplifying a nucleotide sequence set forth in SEQ ID NO:3 to obtain a gene encoding 3-ketosteroid-9α-hydroxylase oxidation subunit KshC, and cloning the gene encoding 3-ketosteroid-9α-hydroxylase oxidation subunit KshC to an *Escherichia Coli* expression vector pET- Duet1(+) to obtain a recombinant plasmid pET-Duet1(+)-kshC;
(c) respectively transforming the recombinant plasmids obtained in step (a) and step (b) into *Escherichia Coli* to obtain a recombinant *Escherichia Coli* comprising BL21/pET-28a(+)-kshB and BL21/pET-Duet1(+)-kshC; and
(d) culturing the recombinant *Escherichia Coli* obtained in step (3) to obtain the composition.

9. A method for increasing the efficiency of converting androstane-4-alkene-3,17-diketone to produce 9α-hydroxy androstane-4-alkene-3,17-diketone, which comprises adding 3 ketosteroid -9α-hydroxylase reduction subunit KshB and 3-ketosteroid-9α-hydroxylase oxidation subunit KshC as a catalyst to a biotransformation reaction.

10. The method of claim 8, which further comprises:
(e) rupturing the recombinant *Escherichia Coli* cells to obtain a crude enzyme mixture;
(f) adding an amount of NADH and androstane-4-alkene-3,17-diketone (AD) to the crude enzyme mixture;
(g) incubating the crude enzyme mixture under conditions that support formation of 9α-hydroxy androstane-4-alkene-3,17-diketone from AD; and
(h) adding the 9α-hydroxy androstane-4-alkene-3,17-diketone to a medicine.

11. The composition of claim 1, wherein the genes encoding 3-ketosteroid-9α-hydroxylase reduction subunit KshB and 3-ketosteroid-9α-hydroxylase oxidation subunit KshC are Mycobacterium genes.

\* \* \* \* \*

SEQUENCE LISTING

```
<160> NUMBER OF SEQ ID NOS: 11

<210> SEQ ID NO 1
<211> LENGTH: 1164
<212> TYPE: DNA
<213> ORGANISM: Artificial Sequence
<220> FEATURE:
<223> OTHER INFORMATION: Synthetic DNA

<400> SEQUENCE: 1
atgacgactg agcacgccgg aatccgtgag attgacacag gcgcgttgcc tgatagatac      60
gcgcgcggat ggcactgcct aggaccggtg aagaacttct tagatggcca gccgcatagc     120
gttgagatct tcggcactaa gttagtagta ttcgctgaca ctaaaggtga acttaagatc     180
ttagacggct actgccggca catgggcggt gacctgagcc agggcacgat taagggtgat     240
gaagtagcat gcccgttcca tgactggcgc tggggcggtg acggtaagtg taagttagtg     300
ccgtacgcta agcgcacccc taggttagcg aggactagag cgtggcacac tgacgtgaga     360
ggcgggctgc tcttcgtctg gcatgaccat gaaggtaatg atccacagcc tgaggtgaga     420
atccctgaaa tacctgaggc cgcgtctgat gagtggacgg agtggcagtg gaactccatg     480
ctgatcgagg gctccaactg ccgcgagatc atcgacaacg tgaccgacat ggcccacttc     540
ttctacatcc acttcggcct gccgacctac ttcaagaacg tgttcgaggg ccacatcgcc     600
tcgcaatacc tgcacaacgt gggccgccag gacatcggcg catgggcac gcagtacggc      660 gagagccacc tggactccga ggcgagctac ttcggcccga gcttcatgat caactggctg     720
cacaacaact actccggcta caaggcggag agcatcctga ttaactgcca ctaccgggtc     780
```

| actcaggact ccttcatgct tcagtggggc gtgatcgtcg agaagccgaa gggcatggac | 840 |
| gagaagacca cccagaagct ggccaacgcc atgacggacg cgtcagcca gggcttcctg | 900 |
| caggacgtcg agatctggaa gcacaagacg cgcatcgaca acccgctgct ggtcgaggaa | 960 |
| gacggcgcgg tctaccagat cgccgctgg taccagcagt tctacgtcga cgtggccgac | 1020 |
| atcacccctg acatgaccga ccgcttcgaa atggagatcg acacgaccgc ggccaacgaa | 1080 |
| aagtggcacg tcgaagttga ggagaacctg aagatccagg ccgaacagaa ggcggcggag | 1140 |
| aaggaaaccg ctcaatcaag ctga | 1164 |

<210> SEQ ID NO 2
<211> LENGTH: 1059
<212> TYPE: DNA
<213> ORGANISM: Artificial Sequence
<220> FEATURE:
<223> OTHER INFORMATION: Synthetic DNA

<400> SEQUENCE: 2

| atgactgatg aaccgttagg tagtcacgtt ttagaattgc aggtgagcgc agtgatcgaa | 60 |
| gaaacagcgg atgctagatc attggtgttc gcagtgccgg aaggaagtac tatccctgaa | 120 |
| gatagactga gatatagccc aggtcagttc ttaacattga gagtcccgag tgatagaacc | 180 |
| ggcagtgtgg cccgatgtta cagcttgagt agtagtccag taaccgatga tcaactgacg | 240 |
| gtgacagtga aacgcacagc agatggttac gcaagtaact ggttatgtga taatgcgcac | 300 |
| gcgggtatga aaatgcacgt cttagccccg tcaggtacct tcgtcccgaa agatctggat | 360 |
| acggatttct tactgttggc cgccggaagt ggcatcacac cgatgatggc catctgtaag | 420 |
| tcagctttag cagaaggaag cggtaacgtt gtcttagtgt acgccaatag agatgaaaac | 480 |
| agcgtcatct tcggtgccac cttgagagag ctggcggcaa atatccggga cagattcacc | 540 |
| gttgtgcatt ggttagagac cgtgcagggc ttaccgagtc cggccgccct ggccggcctg | 600 |
| ctggcgccgt acgcgagccg cgaggccttc atctgcggtc cgggcccgtt catggccgcc | 660 |
| gcggagcagg ccctgcagca ggccggcgcg gcggacgagc gcatccacat cgaggtcttc | 720 |
| aagtcgctgg actccgaccc gttcgccgcg gtcgtgatcg aggaagaaga gggcgaccag | 780 |
| gagccggcca ccgcggtcgt caccctggac ggcaccacgc acgaggtccg ctggccgcgt | 840 |
| tccgccaccc tgctggacgt gctgctggac aagggcctgg acgccccgtt ctcctgccgc | 900 |
| gagggccact gcggcgcgtg cgcggtgctg aagaagagcg gcgacgtgga gatgaagatc | 960 |
| aacgacgtcc tggagccgag cgacctggaa gagggcctga tcctgggctg ccaggccacc | 1020 |
| ccggtgtccg acagcgtcga ggtgacctac gacgagtga | 1059 |

<210> SEQ ID NO 3
<211> LENGTH: 1164
<212> TYPE: DNA
<213> ORGANISM: Artificial Sequence
<220> FEATURE:
<223> OTHER INFORMATION: Synthetic DNA

<400> SEQUENCE: 3

| atggccggtc tgaacaacga tagtacaaga gcctcagtca gagaaatcga cgtaggtcaa | 60 |
| ttgccaacac gtttcgcgcg tggatggcat tgtttgggtt tggtgagtga cttcgtagac | 120 |
| ggtcagccgc attcaatcac agctttcggc accaaactgg tagtctttgc cgatagccat | 180 |
| ggtagtgtcc atgttctgga tgcctattgt cgacacctgg tggtgactt aagtcagggt | 240 |
| aaagtcaaag gtgacgccgt cgcgtgcccg ttccatgatt ggcgttgggc gggaaacggt | 300 |

```
agatgcgccc aggtcccgta cgccaagaga gcacctagat tagcgagaac gagagtctgg    360
agaaccagtg tgcgttcagg tctgctgttc gtctggcatg atccggaagg tagtgtgccg    420
agtccgcatc ttgatatccc agatatcccg gaagttaggg accctggttg gaccgagtgg    480
agttggagaa gtgaattaat cggtagcaac tgtagagaaa tcgttgacaa catcgtggat    540
atggcccatt tctattacat ccatttcggt ttcccgacct atttcaaaaa tgtgttcgaa    600
ggtcaagtgg cgtctcagta tctgcgtacc atcggtcgcc cggatgtcca cctgggcggc    660
tcgcactacg ccggcgagca ggtgctggac agcgaggcga gctatttcgg cccgtccttc    720
atgatcaacc gcctgcacaa cagctacagc ggctacgagg tcgaggccat cctggtgaac    780
tgccactacc cggtcacccc ggagagcttc gtcctgcagt ggggcatcat ggtgcgccgc    840
ccgcagggct tgtcagaaga ggccaccgac cgtctgctgc acgccttcac ggagggcgtg    900
tcctccggct tcctgcagga cgtggagatc tggaagaaca agacgcgcat cgacaacccg    960
ctgctggtcg aggaagacgg cccggtctac cagctgcgcc gctggtacga acagttctac   1020
gtcgacgccg ccgacgtgac cccggagatg acggaccgct tcgagtacga ggtcgacacg   1080
accgccgcca acgagtactg cgctccgag  gtcgccgaga acctgcgcca gcgcggcgcc   1140
gcggccgccc cggccagcgg ctga                                          1164
```

<210> SEQ ID NO 4
<211> LENGTH: 352
<212> TYPE: PRT
<213> ORGANISM: Artificial Sequence
<220> FEATURE:
<223> OTHER INFORMATION: Protein translated from synthetic DNA

<400> SEQUENCE: 4

```
Met Thr Asp Glu Pro Leu Gly Ser His Val Leu Glu Leu Gln Val Ser
1               5                   10                  15

Ala Val Ile Glu Glu Thr Ala Asp Ala Arg Ser Leu Val Phe Ala Val
            20                  25                  30

Pro Glu Gly Ser Thr Ile Pro Glu Asp Arg Leu Arg Tyr Ser Pro Gly
        35                  40                  45

Gln Phe Leu Thr Leu Arg Val Pro Ser Asp Arg Thr Gly Ser Val Ala
    50                  55                  60

Arg Cys Tyr Ser Leu Ser Ser Ser Pro Val Thr Asp Gln Leu Thr
65                  70                  75                  80

Val Thr Val Lys Arg Thr Ala Asp Gly Tyr Ala Ser Asn Trp Leu Cys
                85                  90                  95

Asp Asn Ala His Ala Gly Met Lys Met His Val Leu Ala Pro Ser Gly
            100                 105                 110

Thr Phe Val Pro Lys Asp Leu Asp Thr Asp Phe Leu Leu Leu Ala Ala
        115                 120                 125

Gly Ser Gly Ile Thr Pro Met Met Ala Ile Cys Lys Ser Ala Leu Ala
    130                 135                 140

Glu Gly Ser Gly Asn Val Val Leu Val Tyr Ala Asn Arg Asp Glu Asn
145                 150                 155                 160

Ser Val Ile Phe Gly Ala Thr Leu Arg Glu Leu Ala Ala Lys Tyr Pro
                165                 170                 175

Asp Arg Phe Thr Val Val His Trp Leu Glu Thr Val Gln Gly Leu Pro
            180                 185                 190

Ser Pro Ala Ala Leu Ala Gly Leu Leu Ala Pro Tyr Ala Ser Arg Glu
        195                 200                 205
```

Ala Phe Ile Cys Gly Pro Gly Pro Phe Met Ala Ala Glu Gln Ala
    210                 215                 220

Leu Gln Gln Ala Gly Ala Ala Asp Glu Arg Ile His Ile Glu Val Phe
225                 230                 235                 240

Lys Ser Leu Asp Ser Asp Pro Phe Ala Ala Val Val Ile Glu Glu
                245                 250                 255

Glu Gly Asp Gln Glu Pro Ala Thr Ala Val Val Thr Leu Asp Gly Thr
                260                 265                 270

Thr His Glu Val Arg Trp Pro Arg Ser Ala Thr Leu Leu Asp Val Leu
        275                 280                 285

Leu Asp Lys Gly Leu Asp Ala Pro Phe Ser Cys Arg Glu Gly His Cys
    290                 295                 300

Gly Ala Cys Ala Val Leu Lys Lys Ser Gly Asp Val Glu Met Lys Ile
305                 310                 315                 320

Asn Asp Val Leu Glu Pro Ser Asp Leu Glu Glu Gly Leu Ile Leu Gly
                325                 330                 335

Cys Gln Ala Thr Pro Val Ser Asp Ser Val Glu Val Thr Tyr Asp Glu
            340                 345                 350

<210> SEQ ID NO 5
<211> LENGTH: 387
<212> TYPE: PRT
<213> ORGANISM: Artificial Sequence
<220> FEATURE:
<223> OTHER INFORMATION: Protein translated from synthetic DNA

<400> SEQUENCE: 5

Met Ala Gly Leu Asn Asn Asp Ser Thr Arg Ala Ser Val Arg Glu Ile
1               5                   10                  15

Asp Val Gly Gln Leu Pro Thr Arg Phe Ala Arg Gly Trp His Cys Leu
            20                  25                  30

Gly Leu Val Ser Asp Phe Val Asp Gly Gln Pro His Ser Ile Thr Ala
        35                  40                  45

Phe Gly Thr Lys Leu Val Val Phe Ala Asp Ser His Gly Ser Val His
    50                  55                  60

Val Leu Asp Ala Tyr Cys Arg His Leu Gly Gly Asp Leu Ser Gln Gly
65                  70                  75                  80

Lys Val Lys Gly Asp Ala Val Ala Cys Pro Phe His Asp Trp Arg Trp
                85                  90                  95

Ala Gly Asn Gly Arg Cys Ala Gln Val Pro Tyr Ala Lys Arg Ala Pro
            100                 105                 110

Arg Leu Ala Arg Thr Arg Val Trp Arg Thr Ser Val Arg Ser Gly Leu
        115                 120                 125

Leu Phe Val Trp His Asp Pro Glu Gly Ser Val Pro Ser Pro His Leu
    130                 135                 140

Asp Ile Pro Asp Ile Pro Glu Val Arg Asp Pro Gly Trp Thr Glu Trp
145                 150                 155                 160

Ser Trp Arg Ser Glu Leu Ile Gly Ser Asn Cys Arg Glu Ile Val Asp
                165                 170                 175

Asn Ile Val Asp Met Ala His Phe Tyr Tyr Ile His Phe Gly Phe Pro
            180                 185                 190

Thr Tyr Phe Lys Asn Val Phe Glu Gly Gln Val Ala Ser Gln Tyr Leu
        195                 200                 205

Arg Thr Ile Gly Arg Pro Asp Val His Leu Gly Gly Ser His Tyr Ala
    210                 215                 220

-continued

Gly Glu Gln Val Leu Asp Ser Glu Ala Ser Tyr Phe Gly Pro Ser Phe
225                 230                 235                 240

Met Ile Asn Arg Leu His Asn Ser Tyr Ser Gly Tyr Glu Val Glu Ala
            245                 250                 255

Ile Leu Val Asn Cys His Tyr Pro Val Thr Pro Glu Ser Phe Val Leu
        260                 265                 270

Gln Trp Gly Ile Met Val Arg Arg Pro Gln Gly Leu Ser Glu Glu Ala
    275                 280                 285

Thr Asp Arg Leu Leu His Ala Phe Thr Glu Gly Val Ser Ser Gly Phe
290                 295                 300

Leu Gln Asp Val Glu Ile Trp Lys Asn Lys Thr Arg Ile Asp Asn Pro
305                 310                 315                 320

Leu Leu Val Glu Glu Asp Gly Pro Val Tyr Gln Leu Arg Arg Trp Tyr
            325                 330                 335

Glu Gln Phe Tyr Val Asp Ala Ala Asp Val Thr Pro Glu Met Thr Asp
        340                 345                 350

Arg Phe Glu Tyr Glu Val Asp Thr Thr Ala Ala Asn Glu Tyr Trp Arg
    355                 360                 365

Ser Glu Val Ala Glu Asn Leu Arg Gln Arg Gly Ala Ala Ala Ala Pro
370                 375                 380

Ala Ser Gly
385

<210> SEQ ID NO 6
<211> LENGTH: 28
<212> TYPE: DNA
<213> ORGANISM: Artificial Sequence
<220> FEATURE:
<223> OTHER INFORMATION: Synthetic DNA

<400> SEQUENCE: 6
cgggatccat gacgactgag cacgccgg                                  28

<210> SEQ ID NO 7
<211> LENGTH: 30
<212> TYPE: DNA
<213> ORGANISM: Artificial Sequence
<220> FEATURE:
<223> OTHER INFORMATION: Synthetic DNA

<400> SEQUENCE: 7
cccaagcttt cagcttgatt gagcggtttc                                30

<210> SEQ ID NO 8
<211> LENGTH: 31
<212> TYPE: DNA
<213> ORGANISM: Artificial Sequence
<220> FEATURE:
<223> OTHER INFORMATION: Synthetic DNA

<400> SEQUENCE: 8
cgggatccat gactgatgaa ccgttaggta g                              31

<210> SEQ ID NO 9
<211> LENGTH: 30
<212> TYPE: DNA
<213> ORGANISM: Artificial Sequence
<220> FEATURE:
<223> OTHER INFORMATION: Synthetic DNA

<400> SEQUENCE: 9

```
cccaagcttt cactcgtcgt aggtcacctc                                              30

<210> SEQ ID NO 10
<211> LENGTH: 32
<212> TYPE: DNA
<213> ORGANISM: Artificial Sequence
<220> FEATURE:
<223> OTHER INFORMATION: Synthetic DNA

<400> SEQUENCE: 10
cgggatccga tggccggtct gaacaacgat ag                                           32

<210> SEQ ID NO 11
<211> LENGTH: 31
<212> TYPE: DNA
<213> ORGANISM: Artificial Sequence
<220> FEATURE:
<223> OTHER INFORMATION: Synthetic DNA

<400> SEQUENCE: 11
cccaagcttt cagccgctgg ccggggcggc c                                            31
```